United States Patent
Bakhshaee et al.

(10) Patent No.: US 7,445,795 B2
(45) Date of Patent: Nov. 4, 2008

(54) DELIVERY DEVICE, METHOD OF USING AND METHOD OF MANUFACTURING

(75) Inventors: Massoud Bakhshaee, Glasgow (GB); William John Bowtle, Livingston (GB); Alyn Brandon McNaughton, Livingston (GB)

(73) Assignee: MW Encap Limited, West Lothian (GB)

( * ) Notice: Subject to any disclaimer, the term of this patent is extended or adjusted under 35 U.S.C. 154(b) by 474 days.

(21) Appl. No.: 10/296,786

(22) PCT Filed: Jul. 19, 2001

(86) PCT No.: PCT/GB01/03247

§ 371 (c)(1), (2), (4) Date: Nov. 26, 2002

(87) PCT Pub. No.: WO02/07710

PCT Pub. Date: Jan. 31, 2002

(65) Prior Publication Data

US 2003/0150832 A1    Aug. 14, 2003

(30) Foreign Application Priority Data

Jul. 20, 2000    (GB) .................................. 0017673.5
Nov. 21, 2000    (GB) .................................. 0028335.8

(51) Int. Cl.
*A61K 9/48*    (2006.01)
*A61K 9/52*    (2006.01)

(52) U.S. Cl. ....................... 424/451; 424/456; 424/457; 424/463

(58) Field of Classification Search ................. 424/400, 424/451, 452, 455, 456, 457, 458, 463; 514/962, 514/963
See application file for complete search history.

(56) References Cited

U.S. PATENT DOCUMENTS 4,891,172 A * 1/1990 Matsushita et al. ......... 264/4.33

FOREIGN PATENT DOCUMENTS

WO    WO 95/10262    * 5/1995

* cited by examiner

*Primary Examiner*—Johann Richter
*Assistant Examiner*—Konata M George
(74) *Attorney, Agent, or Firm*—Hartman & Hartman, P.C.; Gary M. Hartman; Domenica N. S. Hartman

(57) ABSTRACT

An active principle delivery device (1) comprising an inner capsule (4) within an outer capsule (2), the inner and outer capsules (4,2) containing the same active principle (5,3), with at least the outer capsule (2) being a hard capsule and the active principle (3,5) in at least one of the capsules (2,4), comprising a fluid. Also provided is a method of fabricating such a delivery device (1), as well as a method of controlling the pharmaco-kinetic profile of an active principle.

28 Claims, 2 Drawing Sheets

DELIVERY DEVICE, METHOD OF USING AND METHOD OF MANUFACTURING

CROSS REFERENCE TO RELATED APPLICATIONS

This application claims the benefit of International Application No. PCT/GB01/03247 filed Jul. 19, 2001, having a priority claim to British patent application numbers GB 0017673.5 filed Jul. 20, 2000, and GB 0028335.8 Filed Nov. 21, 2000.

BACKGROUND OF THE INVENTION (1) Field of the Invention

This invention relates to a delivery device and a method of delivering a substance to at least one location, more particularly the invention relates to a delivery device comprising one or more capsules within an outer capsule, with at least two of said capsules containing the same active principle and a method of delivering that active principle.

(2) Description of the Related Art

Capsule technology has been developing for over one hundred years and is now at the stage where many medicaments are formulated so as to be encapsulated within a gelatin capsule. The benefits of such formulations reside in the fact that the capsules are often easy for a patient or other consumer to swallow or use and the capsule can contain a large amount of the particular medicament for delivery to the individual, the actual capsule dissolving in the stomach or other part of the intestinal tract.

Indeed, to ensure that a particular medicament is delivered to the desired site, a large amount of research has been carried out in coating techniques. Such techniques are used to control or at least vary the time or location of dissolution of the capsule and, consequently, the time or location of release of the medicament.

Several known techniques have been developed for the administration of more than one active principle at a time or at short intervals whilst the active principle is in tablet form. In those cases, coatings are also used to vary or control the release time or location of that active principle.

U.S. Pat. No. 1,815,902 (Ellzey) discloses a double capsule, with one capsule within the other, for administering medicaments in which an inner hard gel capsule contains medicament, whilst an outer hard gel capsule contains an innocuous alkaline material.

FR 1454013 (Pluripharm) relates to another type of double capsule with different medicaments, in solid form, in the inner and outer capsules which are made of hard gel, whilst DE 2729068 (Liedtke) is directed to a double capsule in which the same or different active principles in solid form are provided in inner and outer hard gel capsules, with any liquids being provided solely in inner and outer soft gel capsules.

In FR 2524311 (Azalbert), there is described another double capsule for the ingestion of medicinal agents which are different and incompatible with one another. The inner and outer capsules are of hard gel, with the medicinal agents possibly being in liquid form.

EP 0116311 (Morishita Jintan Co et al) teaches a double soft gel capsule with the inner and outer capsules containing different medicines, whilst EP 0130163 (Pharmacia) discloses a double capsule with the inner capsule containing an allergen and the outer capsule containing an antiallergic substance.

U.S. Pat. No. 5,310,555 (Zimmer) is directed to a method of delivering incompatible and different compounds in vivo, with live intestinal or rumen microorganisms in an inner capsule and a nutritional supplement in an outer shell in which the inner capsule is contained.

EP 0624365 (ASTA Medica) describes a form of double capsule arrangement in which an outer sheath has bioadhesive properties and contains a capsule containing at least one hygroscopic substance and non-liquid active agent tablets.

WO 95/10262 (RP Scherer Corporation) relates to a controlled release device for delivering a liquid substance to a patient, wherein different materials are contained in a double capsule. The liquid substance is contained in an inner soft or hard gel capsule and an inert solid excipient is contained in an outer hard gel capsule, with a water-swellable material in the outer capsule for causing disengagement of the capsules upon exposure to an aqueous medium.

WO 99/30693, AXCAN PHARMA shows that it is possible to provide a double capsule for the administration of active medicaments in multiple therapies. This disclosure considers the possibility of treating a microorganism, such as Helicobacter pylori, with known solid medicaments in a double capsule.

The multiple capsule delivery devices discussed above show that is known to provide double, triple and, sometimes, quadruple therapies for the treatment of many conditions, wherein the inner and outer capsules can be provided in certain, but not all, combinations of solid and soft get capsules containing the same or different active principles in solid or liquid form.

However, none of the prior art delivery devices discussed above ever discloses, whether directly or by implication, the use of the same active principle as a fluid, such as liquid or semi-solid, in a particular multiple capsule format for the treatment of a plurality of conditions.

Also, these known multiple capsule delivery devices provide treatment regimes which are limited, as it has been found to be difficult to control and vary the posologies, particularly when solid active principles are employed. Indeed, it is known also that certain active principles are not amenable to patients in solid form and it is well established that the most effective dose of most medicaments occurs when the active principles are in liquid form, for example, as an aqueous solution, suspension, micelle or emulsion.

BRIEF SUMMARY OF THE INVENTION

Accordingly, it is an object of the invention to provide a delivery device which overcomes the problems associated with the known devices of the prior art discussed above. It is also an object to provide a delivery device which can be used in the treatment of a plurality of conditions, where at least one desired form of active principle is fluid and where it is desired to control both the release rate and site of release of the active principle.

Thus, a first aspect of the invention provides an active principle delivery device comprising an inner capsule within an outer capsule, wherein:

the inner and outer capsules contain the same active principle;

at least the outer capsule is a hard capsule; and the active principle in at least one of the capsules comprises a fluid (as hereinafter defined).

A second aspect of the invention resides in a method of fabricating an active principle delivery device, comprising:

providing a first capsule and a second capsule of which at least the first capsule is a hard capsule;

placing the same active principle in each of the first and second capsules, with the active principle in at least one of the capsules comprising a fluid (as hereinafter defined); and placing the second, active principle-containing, capsule within the first, active principle-containing, hard capsule.

In a third aspect of the invention, there is provided a method of controlling the pharmaco-kinetic profile of an active principle comprising:

determining the most efficacious site of active principle release;

placing an active principle in a first hard capsule;

placing the same active principle in a second capsule within the active principle-containing, first hard capsule, with the active principle in at least one of the first and second capsules comprising a fluid (as hereinafter defined), to provide a delivery device;

delivering the delivery device to the predetermined active principle release site; and controlling the release of the active principle at the site.

In preferred embodiment to be described hereinbelow, the active principle is medicinal and/or nutritional.

Throughout this specification, the term "fluid" or derivatives thereof is used to describe a material which is a liquid or a semi-solid but not a gas, a liquid being defined as a material which flows under ambient conditions without external influences, whilst a semi-solid is defined as a material or mixture of material which has a consistency that varies according to its conditions within an ambient range and which may have characteristics of both a liquid and a solid. Examples of semi-solids include creams, pastes, ointments, suspensions, emulsions, thixotrope and waxes. Changes in ambient conditions, such as a temperature change, could alter a semi-solid to a more liquid state, whilst agitation, such as shaking, could change a thixotrope from a more solid state to a more liquid state.

At least a portion of the active principle may be a fluid either at or immediately prior to its time of use or during its manufacture Although the first, outer capsule is a hard capsule, the second, inner capsule may be a hard or soft capsule and each may be constructed from, for example, gelatin, plasticised gelatin, hydroxy propyl methyl cellulose (HPMC), starch or agar. Each of the inner and outer capsules may be coated or uncoated. In a preferred embodiment, the second inner capsule is a hard capsule and the active principle in both the inner and outer capsules comprises a fluid.

Preferably, the fluid is a liquid which may be a solution or suspension and may comprise suspended solids which may be a powder, pellet, or granules and which may be coated or uncoated. The liquid may also be thermosoftening. At least one of the capsules may contain the same active principle in more than one phase, for example, liquid, semi-solid and/or solid phases.

DETAILED DESCRIPTION OF THE INVENTION

The delivery device may comprise more than one second, inner capsule within the first, outer capsule, the second, inner capsules being arranged in parallel and/or in series.

In a preferred embodiment, the delivery device provides a pharmaceutical dosage form for the administration of the same active principle in single therapies.

Also, the device may comprise an activator or co-reactant for the active principle.

BRIEF DESCRIPTION OF THE DRAWINGS

The various aspects of the invention will now be described by way of example only, and with reference to the accompanying drawings in which.

Figure 1:
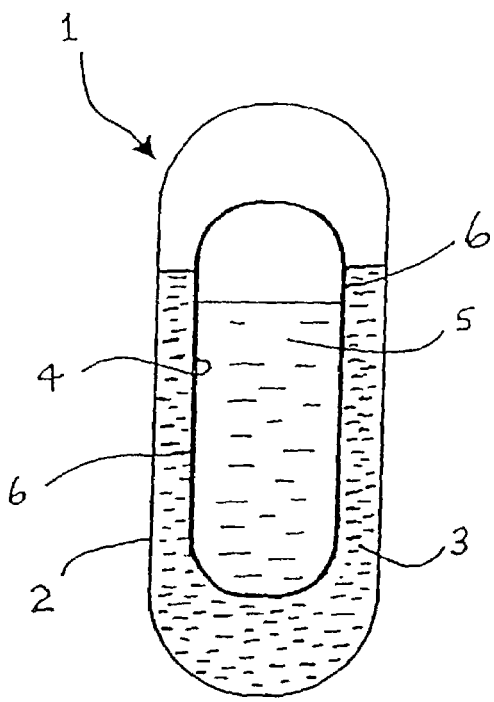
FIG. 1 is a section through a first embodiment of delivery device.

Referring firstly to FIG. 1, a double capsule delivery device, indicated generally at 1, comprises a first, outer hard capsule 2 containing a liquid active principle 3 and a second, inner hard capsule 4 which also contains the same liquid active principle 5 as that contained in the outer hard capsule 2 and may be coated, as shown at 6.

Figure 2:
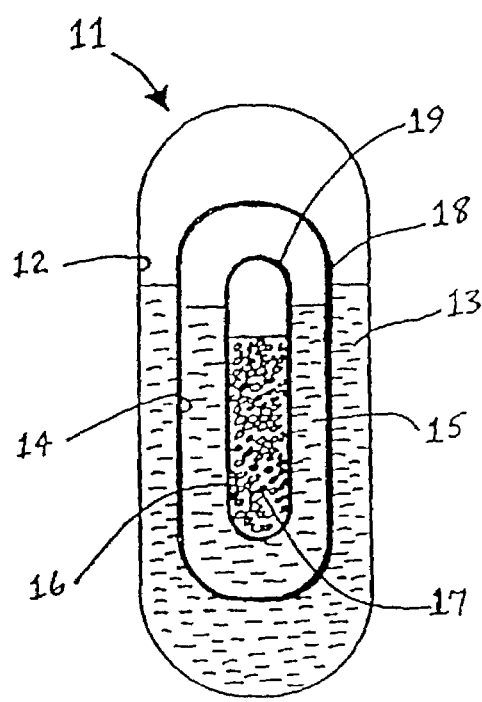
FIG. 2 is a section through a second embodiment of delivery device.

Similarly, FIG. 2 illustrates a triple capsule delivery device, indicated generally at 11, which comprises a first, outer hard capsule 12 containing a liquid active principle 13 and a second, inner hard capsule 14 which also contains the same liquid active principle 15 as that contained in the outer hard capsule 12 and may be coated, as shown at 18. The second, inner hard capsule 14 also contains a third, inner hard capsule 16 which, in turn, contains the same active principle as that contained in the first and second, outer and inner hard capsule 12 and 14 but in solid particulate form. That second, inner hard capsule 14 may also be coated, as shown at 19. The capsules 12, 14 and 16 are in series with each other.

Figure 3:
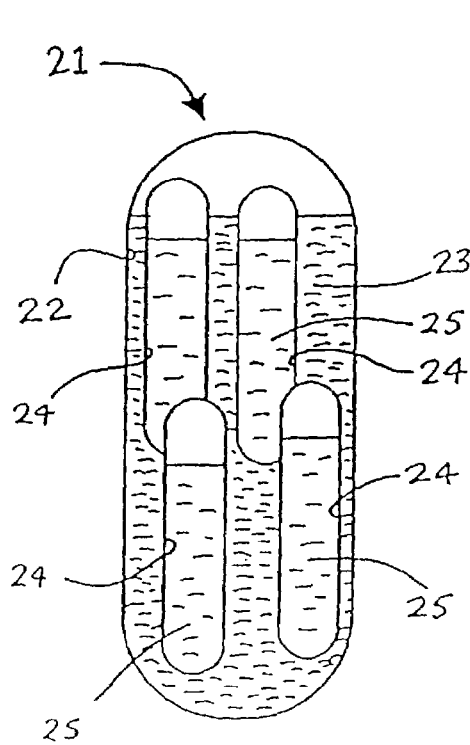
FIG. 3 is a section through a third embodiment of delivery device.

Referring now to FIG. 3, a multiple capsule delivery device, indicated generally at 21, comprises a first, outer hard capsule 22 containing a liquid active principle 23 and four inner hard capsules 24 containing an active principle 25 which is the same as that contained in the first, outer capsule 22 but in semi-solid form. The four inner capsules 24 are in parallel with each other but in series with the outer capsule 22.

Each capsule 2, 4; 12, 14, 16; 22, 24 may be filled using standard capsule-filling technology, such as intermittent or continuous motion capsule filling machines equipped with dosators, to place the same active principle therein. Similar technology may be used to place the inner capsules 4; 14, 16; 24 within the respective outer capsules 2, 12, 22.

Although the first outer capsule 2, 12, 22 is a hard capsule, as are the inner capsules 4; 14, 16; 24 in the three embodiments described above, the inner capsules 4; 14, 16; 24 may be soft capsules. However, any combination of hard and soft inner capsules may be employed. Also, although the first, outer hard capsule 2, 12, 22 of those three embodiments contains the active principle as a liquid, it need not necessarily, as long as at least one of the outer capsules 2, 12, 22 and the inner capsules 4; 14, 16; 24 contains the active principle as a liquid.

The outer hard capsule 2, 12, 22 may be made from any suitable material which will depend upon application requirements. Such materials may include hard gelatin, hydroxy propyl methyl cellulose (HPMC) and starch, whilst any inner capsule 4; 14, 16; 24 which is hard may be made from such a material. Alternatively, and if any inner capsule is a soft capsule, then such may be made from soft gelatin or agar.

It is well established in the medical treatment of ailments, in particular, human ailments, that there are two important thresholds for drugs. The first threshold is the therapeutic threshold, which may be defined as the concentration of active principle at which the principle shows a therapeutic effect on the particular ailment. The second such threshold is the toxic threshold, which occurs when the amount of drug reaches a concentration at which the person who has ingested the drug is, or at least starts to become, poisoned thereby. This effective concentration range between the therapeutic and toxic thresholds may be defined as the activity window.

Active principles, once released, are normally absorbed by the body where they are either metabolised or excreted. Obviously, the balance between release/absorbance rate and removal rate (for example, the sum of the rates of excretion and metabolisation) provides the so-called pharmaco-kinetic profile of a particular active principle. The pharmaco-kinetic profile for a particular active principle may be non-ideal. For example, the concentration of active principle at the desired site may rapidly fall below its therapeutic threshold once released. Alternatively, and as is more usual, the concentration of the drug may slowly reduce to below the therapeutic threshold before sufficient time has elapsed for the active principle to yield the desired result.

A solution to this low active principle concentration problem is simply to administer more of the active principle. However, whilst this may increase the concentration of the active principle and concomitantly the time that the patient's blood contains above the therapeutic threshold, it may also increase the concentration above the toxic threshold, consequently poisoning the person to whom the drug was administered. Indeed, some active principles have very small activity windows and therefore administering large doses of the active principle is undesirable. In such cases, it is usual to prescribe complicated administration regimes wherein a patient is forced to take a large number of relatively small dose drugs frequently. Such regimes are costly and difficult to administer, act to limit or control the patient's freedoms and, moreover, may be difficult to ensure patient's compliance therewith.

Figure 4A:
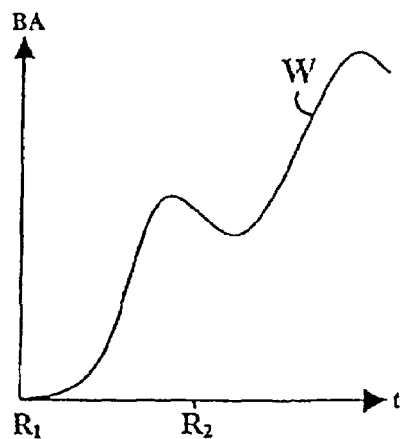
FIGS. 4A to 4D are example representations of pharmaco-kinetic profiles.

With regard now to FIG. 4A, there is shown a pharmaco-kinetic profile W of active principle concentration against time for a particular active principle. The curve W is found after administration of an active principle, in a single therapy, in the form of the delivery device 1, shown in FIG. 1.

The delivery device 1 comprises the outer hard capsule 2 which contains the liquid active principle 3 and which is uncoated and the inner capsule 4 which also contains the same liquid active principle 5 and which is provided with an enteric or erodible coating 6. Once ingested, represented by $R_1$, the outer capsule 2 is quickly broken down and the contents 3 made available, showing an increase in the concentration of the active principle. The coating 6 on the inner capsule 4 prevents immediate release of the contents 5 thereof. However, over time the coating breaks down and, at $R_2$, the contents 5 are released and therefore made available to the body. The effect, as shown in FIG. 4A, is a superposition of two active principle concentration curves to provide the composite pharmaco-kinetic profile W shown.

Figure 4B:
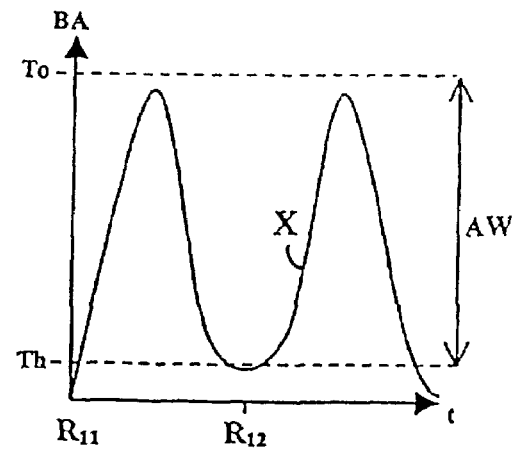

In FIG. 4A, the active principle 3, 5 has a relatively long absorption half-life, which is to say that it is slowly absorbed by the body. In contrast, FIG. 4B shows a situation wherein the active principle 3, 5 has a short absorption half-life and is rapidly absorbed (and eliminated) by the body. A delivery device 1, such as that shown in FIG. 1, may be used and again, the inner capsule 4 is coated at 6 to prevent early release of the active principle 5 contained therein. As can be seen in FIG. 4B, the superposition of the two active principle concentration curves provides a composite pharmaco-kinetic profile X showing the pulsed release of the principle 3, 5. The activity window AW of the same principle 3, 5 is also indicated (AW=toxic threshold (To)–therapeutic threshold (Th)). Such a formulation, as is contained within the delivery device 1, allows for continual administration of an efficacious dose whilst the patient only has to take a single capsule.

Obviously, a delivery device 11 such as that shown in FIG. 2 could also be configured to provide pulsed release of a principle. In such a device 11 the intermediate capsule 14 may be coated at 18 to prevent immediate release, as may the inner capsule 16 at 19, the effect being a "three-pulse" system in which the active principle 13, 15, 17 is delivered, or at least made available, in a controlled fashion. Moreover, with a surreptitious choice of coatings 18, 19, a so-called "parallel" device 21 as shown in FIG. 3 could also be used.

Figure 4C:
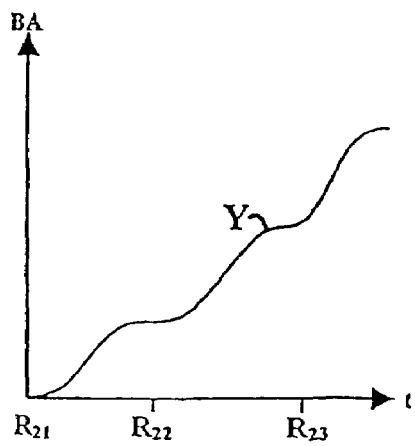

FIG. 4C shows a composite pharmaco-kinetic profile Y in which sustained release of the active principle is described. The delivery devices 11, 21 may be arranged to provide such a profile Y. In some cases, a large dose of a principle is required although the body may not respond positively to a large immediate dose. Thus the active principle concentration is "ramped-up" slowly by sequential release of active principle from sequential breakdown of the capsules. In FIG. 4C, three releases $R_{21}, R_{22}, R_{23}$ are indicated. With certain medicaments, the toxicity threshold To may increase once the body has adjusted to the initial dose. In such circumstances, it is beneficial to provide sequential release of the active principle, taking advantage of the patient's increased tolerance thereof.

Figure 4D:
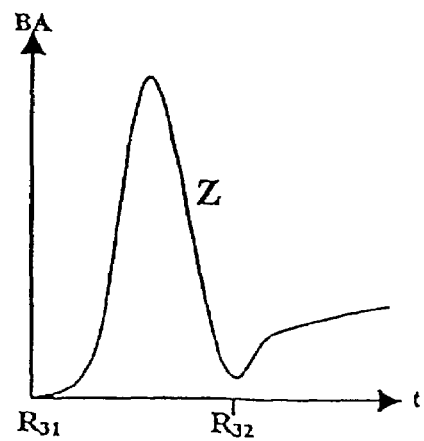

FIG. 4D shows a representation of a further composite pharmaco-kinetic profile Z in which two releases $R_{31}, R_{32}$ are indicated. The first release $R_{31}$ shows a rapid rise in active principle concentration which equally rapidly dies away, the second release $R_{32}$ providing a sustained release of active principle. This matched acute and chronic release profile provides a composite pharmaco-kinetic profile Z in which the patient is exposed to a large initial concentration of active principle followed by a sustained increase in active principle concentration. Such a profile Z may be desirable in circumstance where the initial dose primes the patient for a more sustained dose. Both serial and parallel devices 1, 11, 21 may be utilised to provide such a profile, with careful consideration being given to the choice of coatings 6, 18, 19 which could be applied to any or all of the capsules 2, 4; 12, 14, 16; 22, 24.

The FIGS. 4A to 4D show particular pharmaco-kinetic profiles W, X, Y and Z. It will be understood by the skilled addressee that many desired profiles are achievable. For example, it is a simple matter to provide, or at least closely approximate, a steady-state active principle concentration, which is to say an invariant pharmaco-kinetic profile over time, the rate of removal being equal to the rate of release/absorption of active principle. In such a fashion, the gastrointestinal (GI) tract, or at least a portion thereof, may be subjected to an at least approximately constant concentration of active principle as a delivery, device 1, 11, 21 travels therealong, releasing its active principle. Alternatively, a certain portion of the GI tract may be subjected to a steady-state concentration whilst another portion is subjected to a pulse of active principle, for example.

The above discussion has been silent as to the most efficacious site of principle delivery. The delivery devices 1, 11, 21 can be used to deliver their contents to the most efficacious site in the gastrointestinal (GI) tract. For example, certain active principles may not be best suited for uptake from the acidic conditions prevalent in the stomach and may be best suited for up-take in the colon. In such circumstance the capsules can be coated such that they are only slowly dissolved under strongly acidic conditions, thereby bypassing the stomach.

Moreover, it may be desirable to deliver an active principle to more than one site in the GI tract, for example the stomach and the colon. For such a delivery regime, the inner capsule 4 may be provided with a coating which slowly dissolves once exposed to the conditions of the stomach, the outer capsule 2 having been dissolved soon after ingestion. In this case, the coating is arranged to dissolve, under the prevailing conditions, in the time taken for the device 1 to travel from the stomach to the desired delivery site. A typical release profile may be shown by the pharmaco-kinetic profile Z of FIG. 4D in which the first release $R_{31}$ occurs in the stomach and the second release $R_{32}$ occurs further down the GI tract, for example in the colon. As is shown, the active principle concentration in the stomach and colon of the active principle are distinct due to the differing environmental conditions, the desired treatment regime and the efficacy of the active principle in each location.

An example of the potential uses of such a regime is in the treatment of excess dissolved intestinal gases. Intestinal wind is, in the main, caused by the swallowing of air whilst eating and drinking together with the small amount which is formed through the bi-products of bacterial digestion within the stomach and GI tract. These gases become dissolved in the stomach contents and can cause discomfort, in some cases pain, and embarrassment. The usual way to treat such an ailment is to provide medicaments such as simethicone or dimethicone which reduce the surface tension of the stomach GI tract contents, allowing the dissolved gases to come out of solution and be released from the body. Whilst the problem of dissolved gases can be addressed in the stomach it is conventionally relatively difficult to treat the problem lower in the GI tract without using high doses. The delivery device 1 may be used to do so, in the manner discussed above with a lower dose of the active principle.

A further method of altering the release rate, and thus the absorbance profile, of an active principle, is to provide the same active principle in a two or more different and distinct phases, for example solid and liquid within a single capsule. For example, the delivery device 1 of FIG. 1 may comprise an uncoated outer capsule 2 in which is situated a liquid active principle 3 and a coated inner capsule 4. The inner capsule 4 may contain the same active principle 5 in, for example, an aqueous liquid formulation and a coated solid, such as pellet, formulation. The encapsulated active principle could also be thermosoftening, which is to say that as the temperature increases the viscosity of the active principle decreases.

Once the outer capsule 2 has dissolved and the contents 3 thereof have been absorbed, the inner capsule 4 starts to dissolve. Once this has occurred the aqueous liquid formulation of the active principle 5 is rapidly absorbed whilst the coating on the pellets is dissolving. As that coating dissolves, the solid formulation of the active principle is absorbed by the patient providing a double pulse and sustained release composite pharmaco-kinetic profile.

Such delivery devices 1; 11; 21 may also be used to separate immiscible components. For example, in certain therapies it is beneficial to deliver the same active principle in a variety of solvents. Such solvents may be water and lipids or fats, the inner capsule 4 containing, for example, an aqueous liquid formulation of the active principle 5 and the outer capsule 2 containing a lipidic formulation of the same active principle 3. These same principles 3, 5 may be delivered to the same or different sites within the body as the treatment necessitates and which delivery sites may be controlled by a coating on the capsules 2, 4.

Thus, it can be seen that with an adroit choice of coating and/or by consideration of the capsules dissolution profile, which is to say the rate at which the capsule dissolves, the delivery device 1; 11; 21 can be arranged to provide the desired pharmaco-kinetic profile for treatment of a particular ailment. This can also be augmented by the provision of the same active principle in a particular phase or in particular phases within each capsule. The provision of serial and parallel arrangements of capsules within a delivery device may also be utilised to control or vary the release of active principle.

In further embodiments, the delivery device, for example 1, may comprise further active principles together with the same primary principle. For example, the outer capsule 2 may contain a main active principle 3 together with another, second active principle, whereas inner capsule 4 may contain the same main active principle 5 and a further, third active principle, main principles 3 and 5 being the same in the same or different phases. The above-identified second and third active principles may inhibit each others activity or it may be desirable to treat a different site within the GI tract with each or they may act synergistically in an undesired fashion. The delivery device 1 affords a clinician the ability to provide all three principles in one delivery device, whilst pre-determining the active principle release profiles and the site of release. This leads to directed treatment of one or more specific ailments, allowing medical staff to accurately target delivery sites and ensure that the active principle concentration is optimum.

It is known that different shell materials exhibit a wide-range of properties. For example, gelatin capsules show an excellent resistance to oxygen penetration but are readily embrittled by the loss of moisture therefrom. However, HPMC capsules are readily penetrated by oxygen whilst being very resistant to moisture embrittlement. Therefore, an oxygen sensitive active principle could be encapsulated within an inner gelatin capsule 4 which is in turn encapsulated within an outer HPMC capsule 2 containing, for example, a non oxygen sensitive formulation. The HPMC outer capsule 2 provides a flexible tough outer shell whilst the brittle inner gelatin capsule 4, which is protected by support from the surrounding active principle, provides protection against oxidation of its contents.

It has been demonstrated that the delivery devices 1; 11; 21 allow for a flexibility of delivery of an active principle. By a simple choice of capsule materials, together with manipulation of capsule coating and or formulation of the active principle it is possible to accurately and precisely target active principle delivery site and concentration. It also allows for incompatible substances to be separated until such times as they are released or, indeed, to keep substances completely separated, delivering said principles to distinct sites.

Moreover, it allows for the simplification of a treatment regime. The delivery devices 1; 11; 21 provide means for controlling complicated treatment regimes and removing some or all of the onus from the patient. In some therapies, cocktails of drugs are prescribed which have to be taken at set times, after meals for example, or in pre-determined patterns. Use of the inventive delivery devices 1; 11; 21 allows for drastic simplification of that procedure which may have profound effects in, for example, rural locations of developing countries where literacy rates may be low and clinicians are not on hand to supervise every aspect of a patient's treatment.

Moreover, in the treatment of animals such simplification of administration regimes is desired. For example, it may be difficult or arduous to repetitively administer medicaments to animals to treat a particular complaint. The inventive delivery devices 1; 11; 21 provide means to simplify that procedure, ensuring that the animal receives the desired dose of medicament whilst minimising the number of times a vet, for example, has to visit the animal and simplifying the treatment regime.

In, certain medical or other uses, time and one or more prevailing environmental conditions may affect the release rate. For example, the acidity of the stomach may partially control the release rate.

It is clear, therefore, that the inventive delivery devices 1; 11; 21 and associated methods provide means of delivering active principles and other components to a desired site by control of a few simple parameters. It should be understood that although the invention has been described with reference to the above examples, the ambit of the invention is to be determined by the appended claims.

It is to be appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. An active principle delivery device for controlling a release rate and delivery site of a medicinal and/or nutritional active principle, the delivery device being formed from fillable outer and inner capsules, the outer capsule containing the active principle, the inner capsule within the outer capsule also containing the active principle, at least the outer capsule being a hard capsule, and the active principle in at least the outer capsule comprising a fluid;
    wherein the active principle contained by at least the outer capsule is a liquid either at or immediately prior to its time of use or during its manufacture;
    wherein the liquid comprises a solution and/or a suspension of the active principle; and
    wherein the liquid is thermosoftening.

2. An active principle delivery device for controlling a release rate and delivery site of a medicinal and/or nutritional active principle, the delivery device being formed from fillable outer and inner capsules, the outer capsule containing the active principle, the inner capsule within the outer capsule also containing the active principle, at least the outer capsule being a hard capsule, and the active principle in at least the outer capsule comprising a fluid;
    wherein at least the outer capsule consists of a material selected from the group consisting of gelatin, plasticised gelatin, hydroxy propyl methyl cellulose, starch, and agar.

3. An active principle delivery device for controlling a release rate and delivery site of a medicinal and/or nutritional active principle, the delivery device being formed from fillable outer and inner capsules, the outer capsule containing the active principle, the inner capsule within the outer capsule also containing the active principle, at least the outer capsule being a hard capsule, and the active principle in at least the outer capsule comprising a fluid;
    wherein at least one of the inner and outer capsules is coated or uncoated in accordance with a desired release profile of the active principle.

4. An active principle delivery device for controlling a release rate and delivery site of a medicinal and/or nutritional active principle, the delivery device being formed from fillable outer and inner capsules, the outer capsule containing the active principle, the inner capsule within the outer capsule also containing the active principle, at least the outer capsule being a hard capsule, and the active principle in at least the outer capsule comprising a fluid;
    wherein the active principle comprises a fluid-suspended solid.

5. A delivery device according to claim 4, wherein the fluid-suspended solid consists of a member selected from the group consisting of a powder, a pellet, and granules.

6. A delivery device according to claim 4, wherein the fluid-suspended solid is coated or uncoated in accordance with a desired release profile of the active principle.

7. A delivery device according to claim 5, wherein the fluid-suspended solid is coated or uncoated in accordance with a desired release profile of the active principle.

8. An active principle delivery device for controlling a release rate and delivery site of a medicinal and/or nutritional active principle, the delivery device being formed from fillable outer and inner capsules, the outer capsule containing the active principle, the inner capsule within the outer capsule also containing the active principle, at least the outer capsule being a hard capsule, and the active principle in at least the outer capsule comprising a fluid;
    wherein at least one of the inner and outer capsules contains the active principle in more than one phase.

9. An active principle delivery device for controlling a release rate and delivery site of a medicinal and/or nutritional active principle, the delivery device being formed from fillable outer and inner capsules, the outer capsule containing the active principle, the inner capsule within the outer capsule also containing the active principle, at least the outer capsule being a hard capsule, and the active principle in at least the outer capsule comprising a fluid, the delivery device comprising more than one inner capsule within the outer capsule, the inner capsules being arranged in parallel with each other.

10. An active principle delivery device for controlling a release rate and delivery site of a medicinal and/or nutritional active principle, the delivery device being formed from fillable outer and inner capsules, the outer capsule containing the active principle, the inner capsule within the outer capsule also containing the active principle, at least the outer capsule being a hard capsule, and the active principle in at least the outer capsule comprising a fluid, the delivery device comprising more than one inner capsule within the outer capsule, the inner capsule being arranged in series with each other.

11. An active principle delivery device for controlling a release rate and delivery site of a medicinal and/or nutritional active principle, the delivery device being formed from fillable outer and inner capsules, the outer capsule containing the active principle, the inner capsule within the outer capsule also containing the active principle, at least the outer capsule being a hard capsule, and the active principle in at least the outer capsule comprising a fluid, the delivery device further comprising an activator or co-reactant for the active principle.

12. A method of fabricating an active principle delivery device, the method comprising the steps of:
    providing fillable first and second capsules of which at least the first capsule is a hard capsule;
    placing an identical active principle in each of the first and second capsules, with the active principle in at least the outer capsule comprising a fluid; and
    placing the second capsule within the first capsule;
    wherein at least the first capsule consists of a material selected from the group consisting of gelatin, plasticized gelatin, hydroxy propyl methyl cellulose, starch, and agar.

13. A method of fabricating an active principle delivery device, the method comprising the steps of:
    providing fillable first and second capsules of which at least the first capsule is a hard capsule;
    placing an identical active principle in each of the first and second capsules, with the active principle in at least the outer capsule comprising a fluid; and placing the second capsule within the first capsule;
wherein at least one of the first and second capsules is coated or uncoated in accordance with a desired release profile of the active principle.

14. A method of fabricating an active principle delivery device, the method comprising the steps of:
providing fillable first and second capsules of which at least the first capsule is a hard capsule;
placing an identical active principle in each of the first and second capsules, with the active principle in at least the outer capsule comprising a fluid; and
placing the second capsule within the first capsule;
wherein the liquid is thermosoftening and comprises a solution and/or a suspension of the active principle.

15. A method of fabricating an active principle delivery device, the method comprising the steps of:
providing fillable first and second capsules of which at least the first capsule is a hard capsule;
placing an identical active principle in each of the first and second capsules, with the active principle in at least the outer capsule comprising a fluid; and
placing the second capsule within the first capsule;
wherein the active principle comprises a fluid-suspended solid.

16. A method according to claim 15, wherein the fluid-suspended solid consists of a member selected from the group consisting of a powder, a pellet, and granules.

17. A method according to claim 15, further comprising the step of formulating a desired release profile of the active principle and providing the suspended solid in coated or uncoated form, such that the release thereof accords with the desired release profile.

18. A method according to claim 16, further comprising the step of formulating a desired release profile of the active principle and providing the suspended solid in coated or uncoated form, such that the release thereof accords with the desired release profile.

19. A method according to claim 17, wherein the desired release profile is determined by a nominal or theoretical pharmaco-kinetic profile of the active principle.

20. A method according to claim 18, wherein the desired release profile is determined by a nominal or theoretical pharmaco-kinetic profile of the active principle.

21. A method of fabricating an active principle delivery device, the method comprising the steps of:
providing fillable first and second capsules of which at least the first capsule is a hard capsule;
placing an identical active principle in each of the first and second capsules, with the active principle in at least the outer capsule comprising a fluid; and
placing the second capsule within the first capsule;
wherein at least one of the first and second capsules contains the active principle in more than one phase.

22. A method of fabricating an active principle delivery device, the method comprising the steps of:
providing fillable first and second capsules of which at least the first capsule is a hard capsule;
placing an identical active principle in each of the first and second capsules, with the active principle in at least the outer capsule comprising a fluid; and
placing the second capsule within the first capsule;
wherein more than one second capsule is placed within the first capsule, the second capsules being arranged in parallel with each other.

23. A method of fabricating an active principle delivery device, the method comprising the steps of:
providing fillable first and second capsules of which at least the first capsule is a hard capsule;
placing an identical active principle in each of the first and second capsules, with the active principle in at least the outer capsule comprising a fluid; and
placing the second capsule within the first capsule;
wherein more than one second capsule is placed within the first capsule, the second capsules being arranged in series with each other.

24. A method of fabricating an active principle delivery device, the method comprising the steps of:
providing fillable first and second capsules of which at least the first capsule is a hard capsule;
placing an identical active principle in each of the first and second capsules, with the active principle in at least the outer capsule comprising a fluid; and
placing the second capsule within the first capsule;
further comprising the step of providing an activator or co-reactant for the active principle within the delivery device.

25. A method of controlling the pharmaco-kinetic profile of an active principle, the method comprising the steps of:
determining a first efficacious site for active principle release;
placing an active principle in a first hard fillable capsule;
placing the same active principle in a second fillable capsule within the first hard fillable capsule, with the active principle in at least the first hard fillable capsule comprising a fluid;
delivering the delivery device to the predetermined site; and
controlling the release of the active principle at the site.

26. A method according to claim 25, further comprising the steps of:
determining a second efficacious site for the active principle release;
delivering at least a portion of the delivery device to the second site subsequent to the delivery of the device to the first site; and
controlling the release of the active principle at the second site.

27. A method according to claim 25, wherein the active principle comprises a medicinal or nutritional product.

28. A method according to claim 25, wherein the control of the release of the active principle is afforded by the dissolution characteristics of at least one of the first hard fillable capsule and the second fillable capsule.

* * * * *